United States Patent
De La Prieta et al.

(10) Patent No.: US 6,613,207 B1
(45) Date of Patent: Sep. 2, 2003

(54) ELECTROCHEMICAL SENSOR FOR ASCERTAINING GAS CONCENTRATIONS IN GASES

(75) Inventors: Claudio De La Prieta, Stuttgart (DE); Jens Stefan Schneider, Anderson, SC (US); Carsten Springhorn, Stuttgart (DE); Thomas Schulte, Stuttgart (DE); Olaf Jach, Boeblingen (DE); Ulrich Eisele, Stuttgart (DE); Carmen Schmiedel, Marbach Am Neckar (DE); Lothar Diehl, Stuttgart (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 09/460,465

(22) Filed: Dec. 14, 1999

(51) Int. Cl.$^7$ ............................................. G01N 27/407
(52) U.S. Cl. ..................... 204/426; 204/408; 204/427
(58) Field of Search ................................ 204/421–429, 204/408

(56) References Cited

U.S. PATENT DOCUMENTS

| | | | | |
|---|---|---|---|---|
| 4,110,260 A | * | 8/1978 | Yamamoto et al. ...... | 252/521.1 |
| 4,121,988 A | * | 10/1978 | Sano et al. ................... | 204/426 |
| 4,197,362 A | * | 4/1980 | Schmidberger ........... | 252/521.1 |
| 4,839,019 A | * | 6/1989 | Takahama et al. ........... | 204/426 |
| 5,037,525 A | * | 8/1991 | Badwal ....................... | 204/421 |
| 5,529,677 A | * | 6/1996 | Schneider et al. .......... | 204/426 |
| 5,582,699 A | * | 12/1996 | Melzer ........................ | 204/420 |

FOREIGN PATENT DOCUMENTS

| | | | |
|---|---|---|---|
| DE | 31 20 159 | | 12/1982 |
| EP | 0125069 | * | 6/1988 |
| GB | 667471 | * | 3/1952 |

* cited by examiner

*Primary Examiner*—T. Tung
(74) *Attorney, Agent, or Firm*—Kenyon & Kenyon

(57) ABSTRACT

An electrochemical sensor for ascertaining gas concentrations in gases, particularly in exhaust gases of combustion engines, includes an oxygen-ion-conductive solid electrolyte which is provided with electrode layers arranged at a distance from one another and with at least one resistance heating element that is separated from the solid electrolyte by an electrical insulating layer, a foil binder layer being provided between the electrical insulating layer and the solid electrolyte. At least one electron-conductive intermediate layer is provided between the electrode-side electrical insulating layer and the adjacent solid electrolyte.

12 Claims, 2 Drawing Sheets

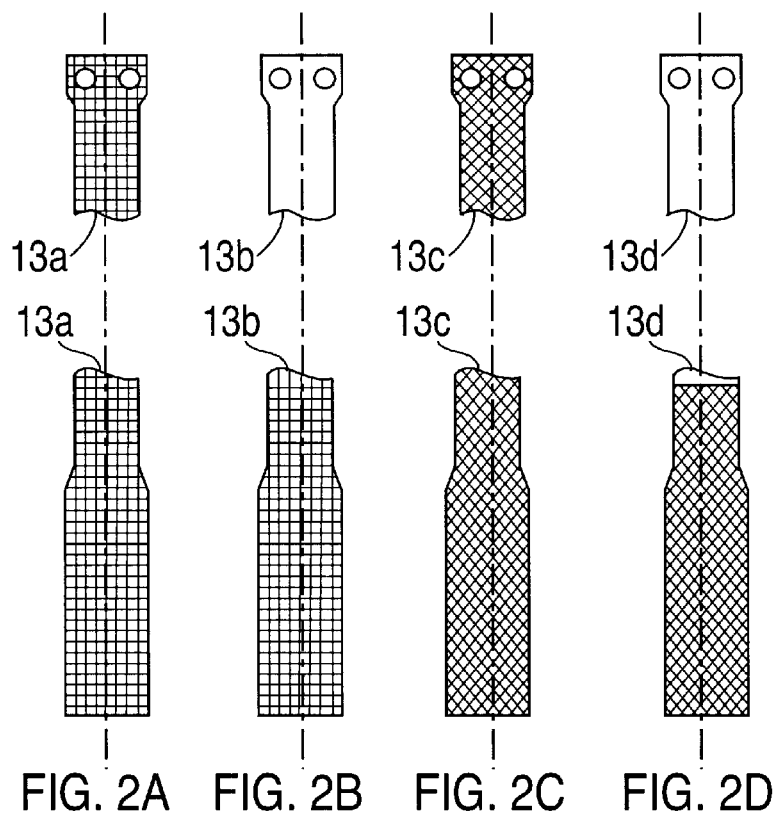
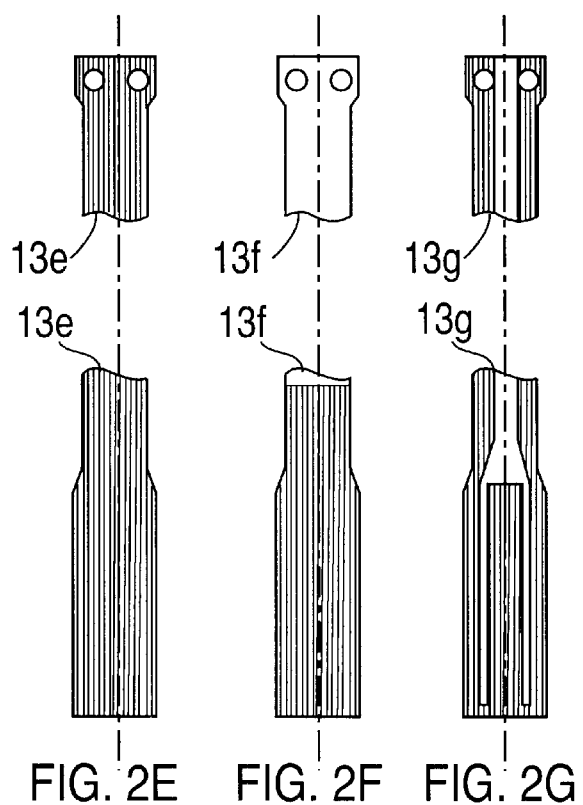
FIG. 2A  FIG. 2B  FIG. 2C  FIG. 2D
FIG. 2E  FIG. 2F  FIG. 2G

ELECTROCHEMICAL SENSOR FOR ASCERTAINING GAS CONCENTRATIONS IN GASES

BACKGROUND INFORMATION

In the electrochemical sensor described in German Pat. No. 31 20 159, the danger exists that during the operation of the heating element, particularly if there is insufficient insulation between the heating element and the oxygen-ion-conductive solid electrolytes which, for example, can be made of yttrium-stabilized $ZrO_2$ (YSZ ceramic), leakage currents will occur which electrically couple the sensor cell to the heating element. First of all, such an electrical coupling reduces the service life of the heater, since reduction effects occur in the active ceramics, and secondly, the measuring signals emitted by the sensor are increasingly and permanently invalidated. Given continuous occurrence, the leakage currents lead to a local blackening of the sensor. In addition, the thin heating lines of the resistance heating element can burn through due to the local heating. In the case of the known sensor, a further disadvantageous effect occurs because of the interspersing of interference signals from the heating element, operated with pulsed voltage, into the probe signal, whereby the measuring accuracy drops because of the reduced signal-to-interference ratio.

SUMMARY OF THE INVENTION

An object of the present invention is to prevent an electrical coupling from the solid-electrolyte sections of the sensor to the heating element during its operation. Furthermore, the intention is to construct a sensor according to the present invention in such a way that blackening no longer occurs during the check for leakage current. Moreover, a sensor of the present invention is to be constructed in a manner that the service life of the heating element is extended. In addition, a sensor according to the present invention should be able to deliver a stable measuring signal over its service life. A sensor of the present invention should also be constructed so that no interference signals from the heating element are interspersed into the measuring-active ceramics, and thus into the sensor signal. A further intention is that the sensor of the present invention be so designed that the accuracy of the measuring signal is improved.

In an electrochemical sensor, designed according to the present invention, for ascertaining gas concentrations in gases, particularly in exhaust gases of internal combustion engines, having an oxygen-ion-conductive solid electrolyte which is provided with electrode layers arranged at a distance from one another and with at least one resistance heating element that is separated from the solid electrolyte by an electrical insulating layer, at least one foil binder layer being provided between the electrical insulating layer(s) and the solid electrolyte, at least one electron-conductive intermediate layer is provided between the electron-side electrical insulating layer and the adjacent solid electrolyte.

In one preferred specific embodiment, the electrochemical sensor of the present invention has a thin electron-conductive metal layer at least above the resistance heating element. This metal layer can either be imprinted flat-spread as a platinum-containing paste at least over the hot region of the sensor, or else can be applied in the form of a platinum lattice structure at least over the hot region of the sensor. Alternatively, the platinum lattice structure or the imprinted layer made of platinum paste can also lie over the entire surface, i.e., over the hot regions and the leads of the resistance heating element.

The platinum lattice structure can have lattice bars running at right angles, i.e., parallel to the edges of the sensor, or else running diagonally at a specific angle.

In one specific embodiment, the electron-conductive intermediate layer, such as the platinum lattice or a platinum mesh, can lie directly over the electrical insulating layer. Alternatively, the electron-conductive intermediate layer, i.e., particularly the platinum lattice or the platinum mesh, can replace or so modify one of the foil binder layers in the sensor that this/these foil binder layer(s) have sufficient electron conductivity. At the same time, the thermal conductivity of the construction counteracts local overheating of the heater.

To reduce or screen off the interference signals coupled in from the resistance heating element, the electron-conductive intermediate layer or intermediate layers, such as the platinum lattice, can be electrically connected to a defined potential, in particular to earth (ground) potential in the sensor.

BRIEF DESCRIPTION OF THE DRAWINGS

FIG. 2A shows schematically and in the form of a plan view, a first embodiment of a metallic electron-conductive intermediate layer according to the present invention.

FIG. 2B shows a second embodiment.

FIG. 2C shows a third embodiment.

FIG. 2D shows a fourth embodiment.

FIG. 2E shows a fifth embodiment.

FIG. 2F shows a sixth embodiment.

FIG. 2G shows a seventh embodiment.

DETAILED DESCRIPTION

Figure 1:
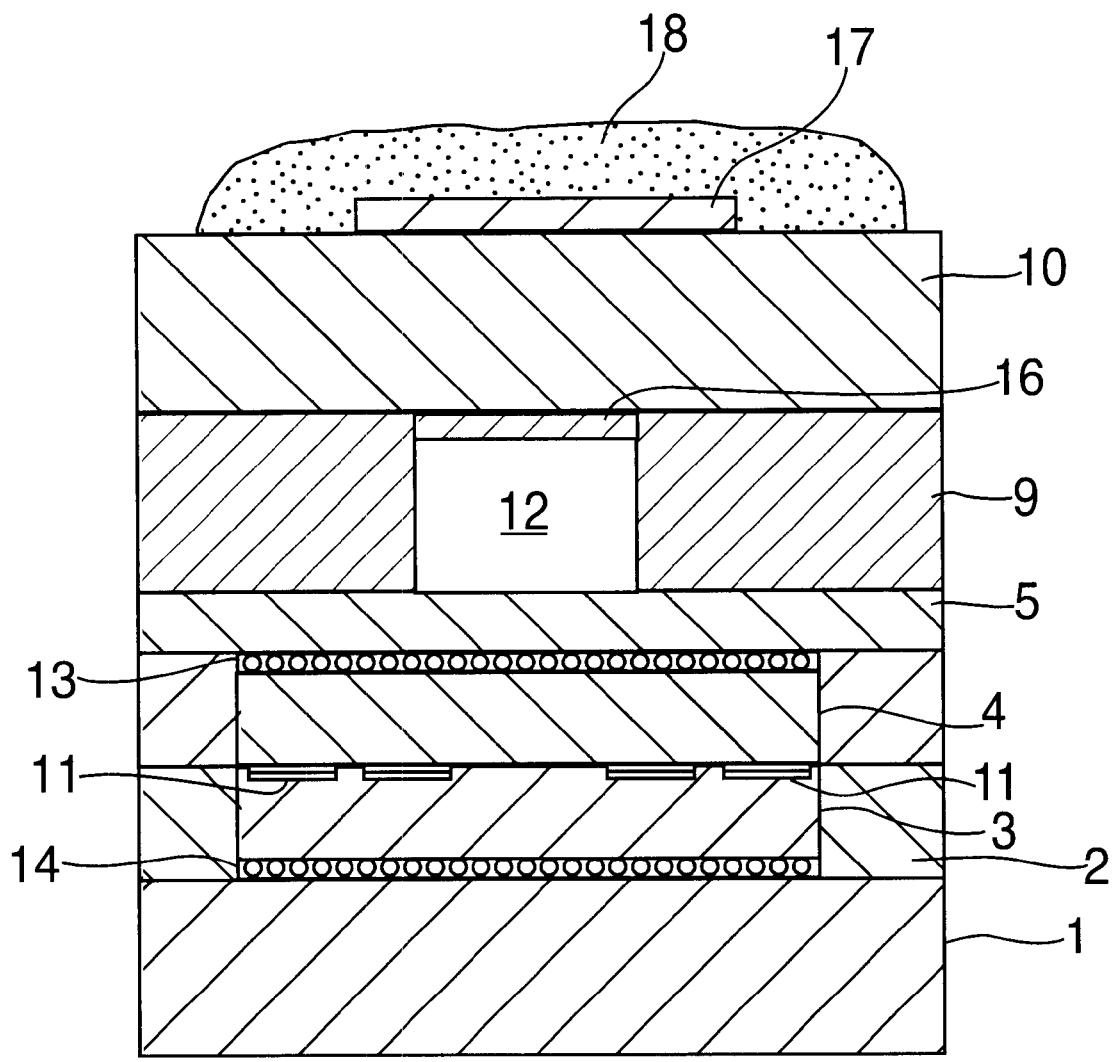
FIG. 1 shows schematically and in section a layer construction of a preferred exemplary embodiment of an electrochemical sensor according to the present invention.

FIG. 1 shows schematically a cross-section through a segment of an electrochemical sensor which embodies a preferred exemplary embodiment of the present invention. It should be noted that the sectional view illustrated in FIG. 1 represents merely the sensor layers located around the heating region made up essentially of a heating foil 1, a heating meander 11 made of electrical resistance material, and electrical insulating, layers 4 (to the top) and 3 (to the bottom) situated around it. Specifically, the electrochemical sensor shown in FIG. 1 is a planar oxygen probe as is used, for example, in the technology of catalytic exhaust emission control of internal combustion engines under the technical designation "planar broad-band lambda probe". The heater, composed of heating meander 11, upper electro-insulating layer 4 and lower electro-insulating layer 3, is mounted with the aid of heating foil 1 on a first solid electrolyte whose details are not further described.

The heater is sealed off on both sides by sealing frame 2 made of $ZrO_2$. Situated over the heater is a foil binder layer 5, and above that, a reference-channel foil 9 which surrounds a reference-gas channel 12 with a reference electrode 16. Above reference-channel foil 9 and reference-gas channel 12 is a Nernst foil 10, made of a solid-electrolyte body, which is possibly also provided with a pump cell (not shown). Lying on Nernst foil 10 is a measuring electrode 17 protected by a protective layer 18. It should be mentioned that insulating layers 3 and 4 are made of a ceramic material, namely, a mixture of $Al_2O_3+SiO_2+BaCO_3$. Heating meander 11 is made of $Pt+Al_2O_3$, and the foil binder is made of $ZrO_2$.

In the exemplary embodiment shown in FIG. 1, situated above upper insulating layer 4, directly below foil binder layer 5, is an electron-conductive intermediate layer 13 made of metallic material, preferably in the form of a platinum lattice or mesh. A further electron-conductive intermediate layer 14 can lie between heater foil 1 and lower insulating layer 3. However, preferably only the upper electron-conductive intermediate layer 13 is provided.

This platinum lattice or mesh can have one of the structures shown in FIGS. 2A through 2D, and according to FIGS. 2A and 2C can either cover the hot region and the leads to the heating element, or only the hot region of the heating element according to FIGS. 2B and 2D.

In a specific embodiment not shown in FIG. 1, electron-conductive intermediate layers 13, 14 are imprinted layers made of a platinum paste and have one of the structures shown in FIGS. 2E–2G.

Deviating from the specific embodiment shown in FIG. 1, the electron-conductive intermediate layer or intermediate layers 13, 14 can have the following variants:

only one, preferably upper electron-conductive intermediate layer 13 is provided;

foil binder layer 5 can be replaced by such an electron-conductive intermediate layer;

the electron-conductive intermediate layer can also be combined in each of these configurations with an ion-conductive intermediate layer, so that both electron and ion conduction occurs in this layer. It should further be mentioned that, in particular to prevent interference signals from being interspersed into the measuring signal, each of electron-conductive intermediate layers 13, 14 in any configuration can be connected to a defined potential, preferably to earth potential, within the sensor.

In the following, various preferred and possible structure variants of a platinum intermediate layer 13 are clarified on the basis of the plan views in FIGS. 2A–2G.

FIG. 2A shows a specific embodiment in which a right-angled platinum lattice structure 13a is placed straight and completely over the heater and its leads. Depending upon the construction, the lattice dimensions can vary from coarse to fine, i.e. approximately between lattice constants (from lattice iine to lattice line) of 0.7 mm to 0.2 mm. Not only quadratic, but also rectangular patterns are possible, in which the lattice constant in the vertical direction differs from the lattice constant in the horizontal direction.

The variant of a platinum lattice 13b shown in FIG. 2B likewise has a right-angled, straight lattice pattern. However, platinum lattice 13b covers only the hot region of the sensor element. The lattice dimensions can be identical to those mentioned for Figure FIG. 2C shows a further structure variant, in which the platinum lattice structure 13c is arranged at a specific angle to the sensor element and is placed completely over the heater and its leads. It can be seen that the structure variant shown in FIG. 2C likewise forms a right-angled lattice. However, this is not necessarily so. Instead of a right-angled or quadratic lattice profile, the lattice lines can also assume an angle deviating from 90° relative to each other. Thus, both rectangular, quadratic, diamond-shaped, and even round and elliptical lattice patterns are possible.

The pattern variant shown in FIG. 2D resembles that in FIG. 2C, however, in this case, lattice 13d covers only the hot region of the sensor element.

In the case of the variants shown in FIGS. 2E, 2F and 2G, electron-conductive intermediate layers 13e, 13f and 13g do not form a lattice or mesh structure as in FIGS. 2A–2D, but rather are applied in the form of a full surface or in the form of broader.platinum strips over the layers of the resistance heating element and its leads. In FIG. 2E, electron-conductive intermediate layer 13e completely covers the heater and the leads; in FIG. 2F, the full surface of electron-conductive intermediate layer 13f is placed only over the hot region of the sensor element; and finally, electron-conductive intermediate layer 13g according to FIG. 2G covers the resistance heating layers of the heater and its leads, so that the resistance layers of the heater are overlapped by electron-conductive intermediate layer 13g.

Common to all the embodiment variants of electron-conductive intermediate layer or intermediate layers 13a–13g shown in FIGS. 2A–2G is that they prevent an electrical coupling from the sensor cell to the heater, thus preventing leakage currents. Blackening is avoided during the leakage-current check. The service life of the heater, and thus of the electrochemical sensor according to the present invention, is extended (longer at least by the factor 5–10). Service life is also extended in the case of sensors without edge grinding (polishing). Reduction effects in the measuring-active ceramic bodies, and thus a change in the sensor characteristics, are prevented. In addition, the platinum functions as a catalyst and converts an electron flow occurring in the insulation into an $O_2$-ion flow in the $ZrO_2$-body, and in this manner decreases the reduction of $ZrO_2$. The electron-conductive intermediate layer or layers also prevent interference signals from being interspersed into the measuring signal, and thus increase its signal-to-interference ratio. In addition, the specific embodiments according to FIGS. 2A–2D, having a lattice net-like pattern of the electron-conductive intermediate layer(s), save on material, i.e., lower costs for raw materials arise during the production of a lattice-type or net-like electron-conductive intermediate layer than when manufacturing a massive platinum intermediate layer.

What is claimed is:

1. An electrochemical sensor for ascertaining a gas concentration in an exhaust gas of an internal combustion engine, comprising:

an oxygen-ion-conductive solid electrolyte provided with electrode layers situated at a preselected distance from one another;

at least one resistance heating element;

at least one electrical insulating layer separating the at least one resistance heating element from the solid electrolyte, the at least one electrical insulating layer including an electrode-side electrical insulating layer;

at least one foil binder layer situated between the at least one electrical insulating layer and the solid electrolyte; and at least one electron-conductive intermediate layer situated between the electrode-side electrical insulating layer and the solid electrolyte, wherein no solid electrolyte layer is situated in a region above the at least one resistance heating element between the at least one resistance heating element and the at least one electron-conductive intermediate layer.

2. The sensor according to claim 1, wherein a first one of the at least one intermediate layer is situated above the at least one resistance heating element.

3. The sensor according to claim 1, wherein the at least one intermediate layer is composed of a metallic material.

4. The sensor according to claim 1, wherein the at least one intermediate layer contains platinum.

5. The sensor according to claim 1, wherein the at least one intermediate layer includes an imprinted layer composed of a platinum paste.

6. The sensor according to claim 1, wherein the at least one intermediate layer forms a platinum lattice structure.

7. The sensor according to claim 1, wherein the at least one resistance heating element includes a hot region and leads, and the at least one intermediate layer covers the hot region and leads.

8. The sensor according to claim 1, wherein the at least one intermediate layer covers only a hot region of the at least one resistance heating element.

9. The sensor according to claim 1, wherein a first one of the at least one intermediate layer lies directly above the electrode-side electrical insulating layer.

10. The sensor according to claim 1, wherein the at least one foil binder layer is electron conductive.

11. The sensor according to claim 1, wherein the at least one intermediate layer is connected electrically to ground in the sensor.

12. An electrochemical sensor for ascertaining a gas concentration in an exhaust gas of an internal combustion engine, comprising:

an oxygen-ion-conductive solid electrolyte provided with electrode layers situated at a preselected distance from one another;

least one resistance heating element;

at least one electrical insulating layer separating the at least one resistance heating element from the solid electrolyte, the at least one electrical insulating layer including an electrode-side electrical insulating layer;

at least one foil binder layer situated between the at least one electrical insulating layer and the solid electrolyte; and at least one electron-conductive intermediate layer situated between the electrode-side electrical insulating layer and the solid electrolyte, the at least one electron-conductive intermediate layer lying directly above the electrode-side electrical insulating layer.

* * * * *

UNITED STATES PATENT AND TRADEMARK OFFICE
CERTIFICATE OF CORRECTION

PATENT NO. : 6,613,207 B1
DATED : September 2, 2003
INVENTOR(S) : Claudio De La Prieta et al.

It is certified that error appears in the above-identified patent and that said Letters Patent is hereby corrected as shown below:

Column 2,
Line 48, change "insulating, layers" to -- insulating layers --.

Column 3,
Line 46, change "lattice iine" to -- lattice line --.
Line 54, change "Figure" to -- Figure 2A --

Column 4,
Line 5, change "broader.platinum" to -- broader platinum --.

Signed and Sealed this

Tenth Day of August, 2004

JON W. DUDAS
*Acting Director of the United States Patent and Trademark Office*